US012703685B2

(12) United States Patent
Repasi et al.

(10) Patent No.: US 12,703,685 B2

(45) Date of Patent: Aug. 11, 2026

(54) CRYSTALLINE FORMS OF SOLVATES OF TRYPTOPHAN DERIVATIVES, COMPOSITIONS COMPRISING THEM AND USES THEREOF

(71) Applicant: GALIMEDIX THERAPEUTICS INC., Kensington, MD (US)

(72) Inventors: Jozsef Repasi, Erd (HU); Andras Szabo, Budapest (HU); Hermann Kurt Russ, Altendorf (CH); Markus Henrich, Münzenberg (DE)

(73) Assignee: Galimedix Therapeutics, Inc.

( * ) Notice: Subject to any disclaimer, the term of this patent is extended or adjusted under 35 U.S.C. 154(b) by 504 days.

(21) Appl. No.: 17/992,961

(22) PCT Filed: May 23, 2021

(86) PCT No.: PCT/IB2021/054469

§ 371 (c)(1),
(2) Date: Nov. 23, 2022

(87) PCT Pub. No.: WO2021/240333

PCT Pub. Date: Dec. 2, 2021

(65) Prior Publication Data

US 2023/0242483 A1 Aug. 3, 2023

Related U.S. Application Data

(60) Provisional application No. 63/029,498, filed on May 24, 2020.

(51) Int. Cl.
*C07D 209/20* (2006.01)

(52) U.S. Cl.
CPC ........ *C07D 209/20* (2013.01); *C07B 2200/13* (2013.01)

(58) Field of Classification Search
CPC .......................... C07D 209/20; C07B 2200/13
See application file for complete search history.

(56) References Cited

U.S. PATENT DOCUMENTS

2006/0234947 A1 10/2006 Gazit
2018/0118682 A1 5/2018 Hauptmeier

FOREIGN PATENT DOCUMENTS

EP 2595625 B1 5/2013
WO WO-2012010415 A1 * 1/2012 .......... A61K 31/305
WO WO-2021/059142 A1 4/2021

OTHER PUBLICATIONS

Bastin et al. (Organic Process Research & Development. 2000; 4: 427-435) (Year: 2000).*
Aaltonen et al. (International Journal of Pharmaceutics. 2008;364:159-169), (Year: 2008).*
(Savonije et al. Brain Sci. Feb. 9, 2023;13(2):292 (Year: 2023).*
Bowker et al. "Preparation of water-soluble compounds through salt formation." The practice of medicinal chemistry. Academic Press, 2008. 747-766.
Brittain "Polymorphism in pharmaceutical solids." Drugs and the pharmaceutical sciences 95 (1999): 183-226.
International Search Report (ISR) from PCT/IB2021/054469.
Jain : "Polymorphism in pharmacy"; Indian Drugs, vol. 23, No. 6, pp. 315-329 Dec. 31, 1986 (Dec. 31, 1986) p. 316.
Parsons et al. "MRZ-99030—A novel modulator of A-beta aggregation: I-Mechanism of action (MoA) underlying the potential neuroprotective treatment of Alzheimer's disease, glaucoma and age-related macular degeneration (AMD)." (2015): 158-69.
Berge, S. M., Bighley, L. D., & Monkhouse, D. C. (1977). Pharmaceutical salts. Journal of pharmaceutical sciences, 66(1), 1-19.
Caira, M. R. (1999). Crystalline polymorphism of organic compounds. In Design of Organic Solids (pp. 163-208). Berlin, Heidelberg: Springer Berlin Heidelberg.

* cited by examiner

*Primary Examiner* — Clinton A Brooks
*Assistant Examiner* — Jerica Katlynn Wilson
(74) *Attorney, Agent, or Firm* — Mark S. Cohen; PEARL COHEN LLP

(57) ABSTRACT

The invention provides crystalline forms of solvates of tryptophan derivatives of compound (1), compositions comprising them, processes for their preparations and methods of use thereof.

13 Claims, No Drawings

CRYSTALLINE FORMS OF SOLVATES OF TRYPTOPHAN DERIVATIVES, COMPOSITIONS COMPRISING THEM AND USES THEREOF

CROSS-REFERENCE TO RELATED APPLICATIONS

This application is a National Phase Application of PCT International Application No. PCT/IB2021/054469, International Filing Date 23 May 2021, claiming the benefit of U.S. Patent Application No. 63/029,498, filed 24 May 2020, which is hereby incorporated by reference.

BACKGROUND OF THE INVENTION

L-tryptophan is an essential heterocyclic amino acid which is part of various naturally occurring peptides. Tryptophan forms a large variety of small peptides. Many of these peptides have physiological activities. Some small peptides (such as Trp-Pro) are known to be useful for the treatment of diseases, e. g. for amyloid-associated diseases, see US 2006/0234947. However, pharmaceutical compositions containing amino acid derivatives often are not stable during storage, in particular when formulated as aqueous solutions. Furthermore, amino acid derivatives used for pharmaceutical compositions often are difficult to purify, hard to solve, and show low bioavailability only. For many pharmaceutical applications, the amount of amino acid derivative needed at the specific site of action is higher than conventional pharmaceutical formulations can provide with.

U.S. Ser. No. 15/848,044 discloses tryptophan derivatives, such as compound (1) and compositions comprising them.

However, these compounds have shown very low solubility in water and organic solvents and have a limited stability as these compounds can cyclize to a diketopiperazine. In addition, most salts of compound (1) are amorphous or glassy (sulfate, hydrogensulfate, phosphate, citrate, mesylate, etc.). The physical state renders these salts useless for pharmaceutical applications. The few crystalline forms of compound (1) exhibited problems such as extensive polymorphism (tartrate) or very poor solubility (free base, acetate or succinate). The most commonly used salt form for APIs in pharmaceutical use, the hydrochloride, also exhibited several concerns from a Good Manufacturing Practice (GMP) and galenic perspective. Depending on the synthesis, the hydrochloride forms a waxy or glassy brownish solid which is unsuitable for pharmaceutical use. Special procedures gave a crystalline salt which did not show the expected stoichiometric ratio of compound (1) versus hydrochloride (1:0.9 instead of 1:1). This means that the compound consists of a mixture of free base and hydrochloride salt. In addition, the salt was not stable over time but lost weight in Differential Thermogravimetry (DTG) experiments, presumably due to further loss of HCl. This instability was already observed at 25° C. which rendered the salt unsuitable for use as a GMP compliant drug substance.

Thus, there is a need to find a solution for improving the purity, bioavailability, solubility, and stability of compounds of formula (I) in order to allow the pharmaceutical composition to be administered safely and efficiently in a proper dose and administration mode to a patient in need thereof.

SUMMARY OF THE INVENTION

The invention provides a novel composition of matter in the form of a crystalline structure of a solvate salt compound (1), wherein said solvate is a $C_3$-$C_4$ alkyl alcohol thereof (1)

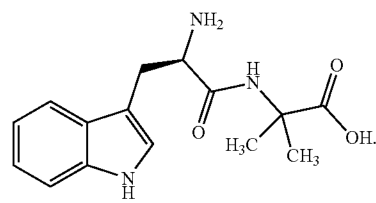

In some embodiments, said salt is an alkali salt. In some embodiments said alkali salt is selected from sodium (Na) and potassium (K).

In some other embodiments said salt of compound (1) is selected from aluminum salt, arginine salt, benzathine salt, ammonium salt, calcium salt, choline salt, diethanolamine salt, ethanolamine salt, ethylenediamine salt, lysine salt, magnesium salt, histidine salt, lithium salt, meglumine salt, procaine salt, triethylamine salt, zinc salt and any combinations thereof.

In other embodiments, said solvate is selected from 1-propanol, 2-propanol, 1-butanol, iso-butanol and any combinations thereof.

Thus, in some embodiments the solvate salt of the invention has the formula (I):

(I)

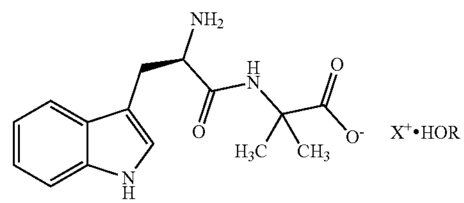

Wherein $X^+$ is an alkali cation; and R is a $C_3$-$C_4$ alkyl. In some embodiments $X^+$ is sodium ($Na^+$) or potassium ($K^+$) cation. In other embodiments, said R is 1-propyl, 2-propyl, 1-butyl, iso-butyl and any combinations thereof.

In further embodiments, said solvate alkali salt compound (1) is a solvated sodium salt selected from:

(2)

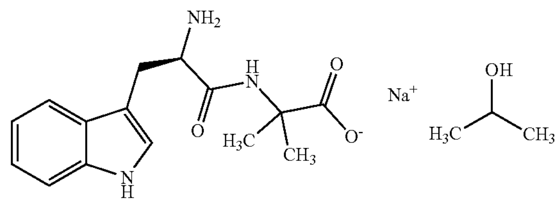

(3)

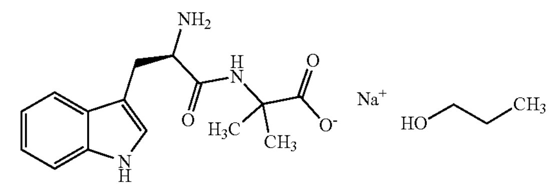

-continued (4)

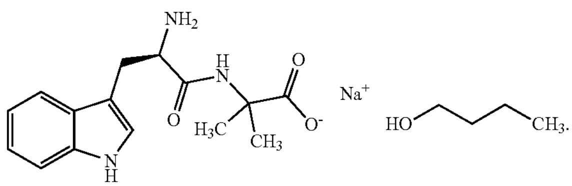

In further embodiments, said solvate alkali salt compound (1) is a solvated potassium ($K^+$) salt selected from:

(5)

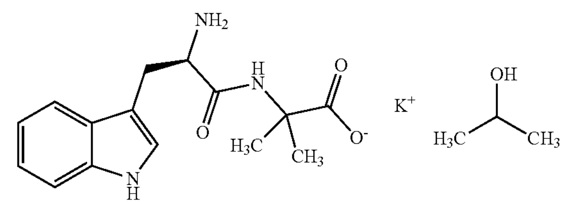

(6)

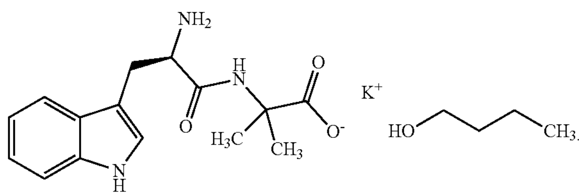

The invention provides a sodium 2-propanol solvate of compound (1) having crystalline form A (the properties of are disclosed herein below).

The invention provides a sodium 1-butanol solvate of compound (1) having crystalline form B (the properties of are disclosed herein below).

The invention provides a sodium 1-propanol solvate of compound (1) having crystalline form C (the properties of are disclosed herein below).

In some embodiments a crystalline form of the invention has purity of at least about 99.7%.

In some embodiments a crystalline form of the invention has water solubility of about 2.3 gr/ml.

The invention further provides a pharmaceutical composition comprising at least one crystalline form of a solvate alkali salt compound (1), wherein said solvate is a $C_3$-$C_4$ alcohol thereof. In some embodiments said solvate alkali salt compound (1) is compound of formula (I).

The invention further provides a pharmaceutical composition comprising at least one crystalline form of a solvate alkali salt compound (1), wherein said solvate is a $C_3$-$C_4$ alcohol thereof; for use in the treatment of an amyloid-associated disease. In some embodiments said solvate alkali salt compound (1) is compound of formula (I).

The invention further provides a method of treating an amyloid-associated disease in a subject suffering therefrom; said method comprising administering to said subject a pharmaceutical composition comprising at least one crystalline form or prepared from at least one crystalline form of a solvate alkali salt compound (1), wherein said solvate is a $C_3$-$C_4$ alcohol thereof. In some embodiments said solvate alkali salt compound (1) is compound of formula (I).

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The invention provides a crystalline form of a solvate salt of compound (1), wherein said solvate is a $C_3$-$C_4$ alcohol thereof (1)

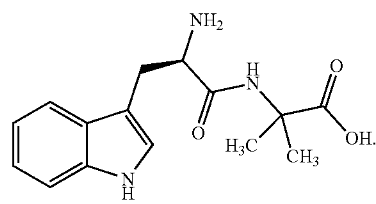

In some embodiments said solvate alkali salt compound (1) is compound of formula (I).

(I)

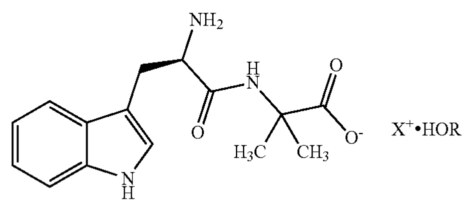

Wherein $X^+$ is an alkali cation; and R is a $C_3$-$C_4$ alkyl. In some embodiments $X^+$ is sodium ($Na^+$) or potassium ($K^+$) cation. In other embodiments, said R is 1-propyl, 2-propyl, 1-butyl, iso-butyl and any combinations thereof.

In some embodiments, said salt is an alkali salt (i.e. the counter cation is an alkali cation). In some embodiments said alkali salt is selected from sodium (Na) salt and potassium (K) salt.

In some other embodiments said salt of compound (1) is selected from aluminum salt, arginine salt, benzathine salt, ammonium salt, calcium salt, choline salt, diethanolamine salt, ethanolamine salt, ethylenediamine salt, lysine salt, magnesium salt, histidine salt, lithium salt, meglumine salt, procaine salt, triethylamine salt, zinc salt and any combinations thereof.

In other embodiments, said solvate is selected from 1-propanol, 2-propanol, 1-butanol, iso-butanol and any combinations thereof.

In some embodiments said $C_3$-$C_4$ alcohol solvate of a crystalline form of the invention may be replaced with one or more of: heptane, acetone, isobutyl acetate, methyl acetate, 2-butanol, 3-methyl-1-butanol, butyl acetate, methylethyl ketone, tert-butylmethyl ether, methylisobutyl ketone, dimethyl sulfoxide, 2-methyl-1-propanol, pentane, 1-pentanol, ethyl ether, ethyl formate, propyl acetate, acetonitrile, chlorobenzene, chloroform, cumene, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, 2-methoxyethanol, methylbutyl ketone, methylcyclohexane, N-methylpyrrolidone, nitromethane, pyridine, sulfolane, tetralin, toluene, 1,1,2-trichloroethene, xylene and any combinations thereof.

Pharmaceutical Compositions

The invention further provides a pharmaceutical composition comprising at least one crystalline form of a solvate alkali salt compound (1), wherein said solvate is a $C_3$-$C_4$ alcohol thereof. In some embodiments said solvate alkali salt of compound (1) is compound of formula (I).

The invention further provides a pharmaceutical composition prepared from at least one crystalline form of a solvate alkali salt compound (1), wherein said solvate is a $C_3$-$C_4$ alcohol thereof. In some embodiments said solvate alkali salt of compound (1) is compound of formula (I).

The invention further provides a pharmaceutical composition comprising at least one crystalline form of a solvate alkali salt compound (1), wherein said solvate is a $C_3$-$C_4$ alcohol thereof; for use in the treatment of an amyloid-associated disease. In some embodiments said solvate alkali salt compound (1) is compound of formula (I).

The invention further provides a pharmaceutical composition prepared from at least one crystalline form of a solvate alkali salt compound (1), wherein said solvate is a $C_3$-$C_4$ alcohol thereof; for use in the treatment of an amyloid-associated disease. In some embodiments said solvate alkali salt compound (1) is compound of formula (I).

Pharmaceutical compositions include those suitable for oral, rectal, nasal, topical (including transdermal, buccal and sublingual), transmucosal, conjunctival, intranasal, vaginal or parenteral (including subcutaneous, intramuscular, intravenous, intramedullar, intrathecal, intraventricular, intraperitoneal, and intradermal), injections into the eye and around the eyeball (including intraocular, periocular, subtenon, intravitreous, intra-anterior eye chamber, subchoroidal, subretinal and intrachoroidal), or administration via an implant. The pharmaceutical compositions may be prepared by any method well known in the art of pharmacy.

Such methods include the step of bringing in association compounds used in the invention or combinations thereof with any auxiliary agent. The auxiliary agent(s), also named accessory ingredient(s), include those conventional in the art, such as carriers, fillers, binders, diluents, disintegrates, lubricants, solubilizers, colorants, flavouring agents, antioxidants, preservatives, viscosity enhancers, and wetting agents.

Pharmaceutical compositions suitable for ocular administration may be presented as eye cream, eye drops, contact lenses, and eye ointments.

Pharmaceutical compositions suitable for intraocular and periocular administration may be presented as intraocular depot formulations.

Pharmaceutical compositions suitable for oral administration may be presented as discrete dosage units such as pills, tablets, pellets, granules, dragées or capsules, or as a powder or granules, or as a solution or suspension. The active ingredient may also be presented as a bolus or paste. The compositions can further be processed into a suppository or enema for rectal administration.

The invention further includes a pharmaceutical composition, as hereinbefore described, in combination with packaging material, including instructions for the use of the composition for a use as hereinbefore described.

For parenteral administration, suitable pharmaceutical compositions include aqueous and non-aqueous sterile injection. The pharmaceutical compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Pharmaceutical compositions or formulations suitable for pulmonary administration e.g. by nasal or oral inhalation include fine dusts or mists which may be generated by means of metered dose pressurized aerosols, nebulisers or insufflators.

In some embodiments, nasal spray composition of the invention is used for the treatment of central nervous system diseases, disorder or symptom thereofs. In other embodiments, nasal drops composition of the invention is used for the treatment of central nervous system diseases, disorder or symptom thereofs. In other embodiments, nasal crème composition of the invention is used for the treatment of central nervous system diseases, disorder or symptom thereofs. In other embodiments, nasal ointment composition of the invention is used for the treatment of central nervous system diseases, disorder or symptom thereofs. In other embodiments, intrathecal injection of the composition of the invention is used for the treatment of central nervous system diseases, disorder or symptom thereofs.

In some embodiments, in cases where the crystalline form of the invention is transformed into a liquid form prior to administration, said composition may be provided in the form of a kit comprising at least one first receptacle comprising a crystalline form of the present invention and at least one second receptacle comprising a pharmaceutically acceptable diluent. A kit of the invention may include instructions for preparation and use of said receptacles for the preparation of an administered dosage form.

Uses

The invention further provides a method of treating an amyloid-associated disease in a subject suffering therefrom; said method comprising administering to said subject a pharmaceutical composition comprising at least one crystalline from of a solvate alkali salt compound (1), wherein said solvate is a $C_3$-$C_4$ alcohol thereof. In some embodiments said solvate alkali salt compound (1) is compound of formula (I).

The invention further provides a method of treating an amyloid-associated disease in a subject suffering therefrom; said method comprising administering to said subject a pharmaceutical composition prepared from at least one crystalline from of a solvate alkali salt compound (1), wherein said solvate is a $C_3$-$C_4$ alcohol thereof. In some embodiments said solvate alkali salt compound (1) is compound of formula (I).

The phrase "amyloid-associated disease or disorder", as used herein, describe a medical condition with a pathology that involves amyloid beta formation, specifically the toxic oligomeric species of amyloid beta. Such a medical condition can involve other pathologies, yet, is treatable, at least to some extent, by reducing, preventing or inhibiting amyloid plaque formation.

In some embodiments, the amyloid-associated disease includes type II diabetes mellitus, Alzheimer's disease (AD), early onset Alzheimer's disease, late onset Alzheimer's disease, Alzheimer's dementia, Parkinson's disease, SAA amyloidosis, hereditary Icelandic syndrome, multiple myeloma, medullary carcinoma, aortic medical amyloid, insulin injection amyloidosis, prion-systematic amyloidosis, chronic inflammation amyloidosis, Huntington's disease, senile systemic amyloidosis, pituitary gland amyloidosis, hereditary renal amyloidosis, familial British dementia, Finnish hereditary amyloidosis, familial non-neuropathic amyloidosis, amyloid-related ocular diseases and disorders such as glaucoma and age-related macular degeneration (AMD, dry form and wet form), prion diseases including prion-related encephalopathies, scrapie of sheep and goats and bovine spongiform encephalopathy (BSE) of cattle and human prion diseases including Kuru disease, Creutzfeldt-Jakob disease (CJD), Gerstmann-Sträussler-Scheinker disease (GSS), and fatal familial insomnia (FFI).

In some embodiments, the ocular diseases and disorder is selected from the group consisting of primary angle-closure glaucoma, secondary open-angle glaucoma, wide-angle glaucoma, steroid-induced glaucoma, traumatic glaucoma, secondary angle-closure glaucoma, neovascular glaucoma, pigmentary dispersion syndrome, pseudo-exfoliation syndrome, uveitis and glaucoma and diabetic retinopathy.

The invention further provides a method of reversing amyloid beta (β) toxicity and rapidly improving function of neuronal, non-neuronal, or neuro-sensory cells, or a combination thereof in a subject; said method comprising administering to said subject a pharmaceutical composition comprising at least one crystalline from of a solvate alkali salt compound (1), wherein said solvate is a $C_3$-$C_4$ alcohol thereof. In some embodiments said solvate alkali salt compound (1) is compound of formula (I).

The invention further provides a method of reversing amyloid beta (β) toxicity and rapidly improving function of neuronal, non-neuronal, or neuro-sensory cells, or a combination thereof in a subject; said method comprising administering to said subject a pharmaceutical composition prepared from at least one crystalline from of a solvate alkali salt compound (1), wherein said solvate is a $C_3$-$C_4$ alcohol thereof. In some embodiments said solvate alkali salt compound (1) is compound of formula (I).

In some embodiments, the neuronal, non-neuronal, or neuro-sensory cells comprise retinal ganglion cells (RGC), retinal pigment epithelium (RPE) cells, photoreceptor photosensory cells comprising rod and cone cells, hippocampal cells, or cortical cells, or a combination thereof.

Dosage

The exact dose and regimen of administration of the pharmaceutical composition will necessarily be dependent upon the therapeutic or nutritional effect to be achieved and may vary with the particular formula, the route of administration, and the age and condition of the individual subject to whom the pharmaceutical composition is to be administered.

Suitable dosage ranges are 1 to 1000 milligrams daily, preferably 5 to 500 milligrams daily, and especially 10 to 200 milligrams daily, depending upon the exact mode of administration, form in which administered, the indication toward which the administration is directed, the subject involved, and the body weight of the subject involved, and the preference and experience of the physician or veterinarian in charge. In one embodiment, the term "therapeutically effective" applied to dose or amount refers to that quantity of a compound or pharmaceutical composition that is sufficient to result in a desired activity upon administration to a living animal body in need thereof.

Suitable dosage ranges for administrations to the eye are in the range of 0.1 mg to 20 mg per single topical application. In other embodiments, Suitable dosage ranges for administrations to the eye are in the range of 0.5 mg to 15 mg per single topical application. In other embodiments, Suitable dosage ranges for administrations to the eye are in the range of 1 mg to 10 mg per single topical application. In other embodiments, Suitable dosage ranges for administrations to the eye are in the range of 2 mg to 6 mg per single topical application. In some embodiment, the applications into the eye are administered once a day, twice a day or three times a day. In some embodiments, the applications into the eye are administered to a maximum of 9 times per day.

In some embodiments a pharmaceutical composition of the invention is formulated for ophthalmic administration (for example drops or kit for preparing drops). In some embodiments the ophthalmic formulation has a concentration of 2%. In other embodiments, the ophthalmic formulation has a concentration of more than about 2%. In other embodiments, the ophthalmic formulation has a concentration of 0.5%-8%. In other embodiments said ophthalmic formulation does not comprise a solubilizer.

In some embodiments a pharmaceutical composition of the invention is an oral administration form. It is noted that the oral availability of the amorphous non solvated crystalline form of compound (1) has poor oral bioavailability (in the range of 5% in rodents only). In some embodiments, the oral availability of the pharmaceutical composition of the invention is in the range of 10%. In another embodiment, the oral availability of the pharmaceutical composition of the invention is above 10%. In some embodiments the pharmaceutical composition is administered once a day, twice a day or three times a day.

In some embodiments, the pharmaceutical composition is administered once every $2^{nd}$ day, once every $3^{rd}$ day, once every $4^{th}$ day, once every $5^{th}$ day, once every $6^{th}$ day, once a week, once a fortnight, once every other week or once a month.

In some embodiments, the pharmaceutical composition is administered as an initial loading dose and further in multiple subsequent maintenance doses.

In some embodiments, the initial dose is administered 1-3 time per day for one day. In other embodiments, the initial dose is given 1-3 time per day for two days. In other embodiments, the initial dose is given 1-3 time per day for three days. In other embodiments, the initial dose is given 1-3 time per day for one week. In other embodiments, the initial dose is given 1-3 time per day for two weeks. In other embodiments, the initial dose is given 1-3 time per day for three weeks. In other embodiments, the initial dose is given 1-3 time per day for one month.

In some embodiments, the maintenance dose is administered once a week. In other embodiments, the maintenance dose is administered twice a week. In other embodiments, the maintenance dose is administered several times a week. In other embodiments, the maintenance dose is administered once every two weeks. In other embodiments, the maintenance dose is administered once every three weeks. In other embodiments, the maintenance dose is administered several times per fortnight. In other embodiments, the maintenance dose is administered once a month. In other embodiments, the maintenance dose is administered several times a month. In other embodiments, the maintenance dose is administered once every two months. In other embodiments, the maintenance dose is administered once every three months.

In some embodiments, the maintenance dose is administered for one month. In other embodiments, the maintenance dose is administered for two months. In other embodiments, the maintenance dose is administered for three months. In other embodiments, the maintenance dose is administered for six months. In other embodiments, the maintenance dose is administered for one year. In other embodiments, the maintenance dose is administered for more than one year.

In some embodiments, the maintenance dose is 10%-75% of the initial dose. In other embodiments, the maintenance dose is 20%-75% of the initial dose. In other embodiments, the maintenance dose is 25%-75% of the initial dose.

In some embodiments, the oral pharmaceutical composition comprises 1 mg-1000 mg of at least one crystalline form of a solvent salt of compound (1). In other embodiments, the oral pharmaceutical composition comprises 5 mg-500 mg of at least one crystalline form of a solvent salt of compound (1). In other embodiments, the oral pharmaceutical composition comprises 10 mg-200 mg of at least one crystalline form of a solvent salt of compound (1). In other embodiments, the oral pharmaceutical composition comprises 50 mg-300 mg of at least one crystalline form of a solvent salt of compound (1). In other embodiments, the oral pharmaceutical composition comprises 100 mg-150 mg of at least one crystalline form of a solvent salt of compound (1). In other embodiments, the oral pharmaceutical composition comprises 150 mg-200 mg of at least one crystalline form of a solvent salt of compound (1).

In some embodiments, administration is in the form of multiple doses administered over a period of time, wherein said time period comprises days, weeks, or months, or at most 1 year. In other embodiments, administration is in the form of multiple doses administered over 1-7 days. In other embodiments, administration is in the form of multiple doses administered over 1-4 weeks. In other embodiments, administration is in the form of multiple doses administered over 1-12 months. In other embodiments, administration is in the form of multiple doses administered over at most 1 year or several over years. In other embodiments, administration is in the form of multiple doses administered over the life-time of the subject. In other embodiments, administration is in the form of multiple doses administered as long as the amyloid β functional toxicity persists, wherein administration is required to reverse the persistence of the toxicity. In other embodiments, administration is in the form of multiple doses administered as long as the amyloid β functional toxicity persists, wherein administration is required to reduce the toxicity.

In some embodiments, the administration of the pharmaceutical composition of the invention will result in higher $C_{max}$ concentration, in comparison to administration of the zwitterionic form with the same applied dose.

The term "treatment" as used herein refers to the administering of a therapeutic amount of the pharmaceutical composition of the present invention which is effective to ameliorate undesired symptoms associated with a disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease form occurring or a combination of two or more of the above.

The "effective amount" for purposes disclosed herein is determined by such considerations as may be known in the art. The amount must be effective to achieve the desired therapeutic effect as described above, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the ligand to the receptor, its distribution profile within the body, a variety of pharmacological parameters such as half-life in the body, on undesired side effects, if any, on factors such as age and gender, etc.

Experimental Section

Potassium and sodium salts of compound (1) (MRZ-99030) were synthetized successfully in solid, amorphous form using aqueous solution of the appropriate alkaline hydroxide followed by lyophilization. The amorphous salts were crystallized from different organic solvent, 2-propanol, 1-propanol and 1-butanol were identified as suitable solvents for crystallization. Larger batches of crystalline salts (~100 g) were prepared starting from the aqueous solution of the sodium salt by azeotropic distillation of water with the certain alcohols followed by crystallization. The obtained crystalline salts have been analyzed by microscope, Differential Scanning calorimetry (DSC) and X-ray Powder Diffraction (XRPD) to check the crystallinity, the composition of the crystals was determined by Nuclear Magnetic Resonance (NMR), water and residual solvent content was measured (Karl Fischer (KF) and Gas Chromatography (HS-GC), respectively), and solubility of the salt in water was also tested.

For the clarification of the designations of compounds in the experimental section:

| Compound | Designated Names | Crystalline Form |
|---|---|---|
| Compound (1) | MRZ-99030; UB-07814; GAL-101; EG-30 | Amorphous |
| Sodium (Na) salt of compound (1) | UB-08090 | Amorphous |
| Sodium (Na) 2-propanol solvate of compound (1) | UB-18813 | Form A |
| Sodium (Na) 1-butanol solvate of compound (1) | UB-18815 | Form B |
| Sodium (Na) 1-propanol solvate of compound (1) | UB-18814 | Form C |
| Potassium (K) salt of compound (1) | UB-08091 | Amorphous |
| Potassium (K) 2-propanol solvate of compound (1) | UB-18816 | Form D |
| Potassoim (K) 1-butanol | UB-18817 | Form E |

Sodium Solvent Salt

In 2-propanol, 1-propanol and 1-butanol at 20-25° C. crystalline salts were obtained with sharp melting point determined by DSC.

Further organic solvents (ethyl acetate (EtOAc), isopropyl acetate (iPrOAC), anisole, tetrahydrofuran (THF), 2-methyl tetrahydrofuran (2-MeTHF), $CH_3CN$) have been investigated but none of them gave crystalline product.

Crystallization was also investigated at 70° C. in 2-propanol, 1-propanol and 1-butanol and compared with the results of room temperature experiments.

The crystalline sodium salt was successfully recovered from aqueous solution by solvent swap to 2-propanol, 1-propanol and 1-butanol using azeotrope distillation. The products were highly crystalline and consisted of one single crystal form (Form A, B and C, respectively).

Water content and residual solvent level was determined (KF and HS-GC), only traces of water were detected in the samples.

Solvent content of the crystalline salts was determined. 1.14-1.18 mol of residual alcohols pro unit was found in the samples indicating the solvate structure of the salts. The slightly higher than 1.0 mol solvent pro unit level suggests that drying was incomplete, not the total amount of the measured solvent is in the crystal lattice.

According to XRPD analysis three crystal forms of the sodium salt were detected (Form A, Form B, and Form C): 2-propanol gave Form A (UB-18813), 1-butanol gave Form B (UB-18815), 1-propanol gave Form C (UB-18814).

All crystal forms have a sharp melting point (determined by DSC), heating the sample above its melting point results in loss of crystal solvent and gives an amorphous sodium salt without decomposition.

The solubility of the sodium salt (Form A) in water was tested. UB-18813 is highly soluble in water, 70 w/w % mixture is a clear, viscous honey-like solution and more salt could be dissolved in the solution. The zwitterionic form of compound (1) (MRZ-99030 or UB-07814) has much lower solubility, concentration of the saturated solution at room temperature is 1.3 w/w %. Stability test of crystalline UB-18813 were performed at 50° C., no degradation was observed after 48 hours. Stability test of 70 w/w % aqueous solution of UB-18813 were performed at 50° C., no degradation was observed within 48 hours. The hygroscopicity of the salt UB-18813 was investigated at 58-60% relative humidity. The weight of crystals increased with 2.64% within 24 hours, 3.4% 48 hours. $^{1}H$- and $^{13}C$-NMR of the salt were recorded

Potassium Solvent Salt

2-Propanol, n-propanol and n-butanol were tested in the crystallization experiments. No crystallization was observed at 20-25° C., clean solution was obtained. After 2 days at −15° C. crystals formed in 2-propanol and n-butanol which did not dissolve at 20-25° C. According to XRPD analysis two crystal forms were detected. (Form D and Form E) (UB-18816 and UB-18817, respectively).

TABLE 1

Crystalline forms and Mw of solvate salts of compound (1)

| Compound | Crystal Form | Sum molecular formula | Molecular weight (g/mol) |
|---|---|---|---|
| Free base of compound (1) | amorphous | $C_{15}H_{19}N_3O_3$ | 289.33 |
| Sodium (Na) 2-propanol solvate of compound (1) | Form A | $C_{18}H_{26}N_3O_4Na$ | 371.41 |
| Sodium (Na) 1-butanol solvate of compound (1) | Form B | $C_{19}H_{28}N_3O_4Na$ | 385.43 |
| Sodium (Na) 1-propanol solvate of compound (1) | Form C | $C_{18}H_{26}N_3O_4Na$ | 371.41 |
| Potassium (K) 2-propanol solvate of compound (1) | Form D | $C_{18}H_{26}N_3O_4K$ | 387.52 |
| Potassium (K) 1-butanol solvate of compound (1) | Form E | $C_{19}H_{28}N_3O_4K$ | 401.54 |

Observations

Surprisingly, sodium and potassium salts of compound (1) (MRZ-99030) are amorphous materials (UB-08090 and UB-08091).

Treating this amorphous salt with alcohols (1-propanol, 2-propanol, 1-butanol) crystalline salt-solvates were obtained. The solvates crystallize in different forms, depending on the solvent used (Form A, B and C) (UB-18813, UB-18814 and UB-18815).

The crystals proved to be solvates with ~1 eq crystal solvent (in case of 2-propanol is stoichiometric, in case of 1-propanol and 1-butanol slightly above the stoichiometry).

Compound (1) is not stable on long term, on storage (even at room temperature) forms the degradation product diketopiperazine. Sodium salt (UB-08090) has much better stability, this is stable at elevated temperature (even at the temperature of its melting point).

The sodium salt of compound (1) (UB-08090) is slightly not hydroscopic, water content increased with 2.6% within 24 hours 3.4% within 48 hours.

While the zwitter ionic form compound (1) crystallizes almost without changes in purity, the salts crystallize with a very high purity, gaining around 1% of purity as compared to the starting material.

Preparation of the Amorphous Sodium Salt of Compound (1) (UB-08090)

Scheme 1 - Synthetic scheme for preparation of sodium salt of compound (1)

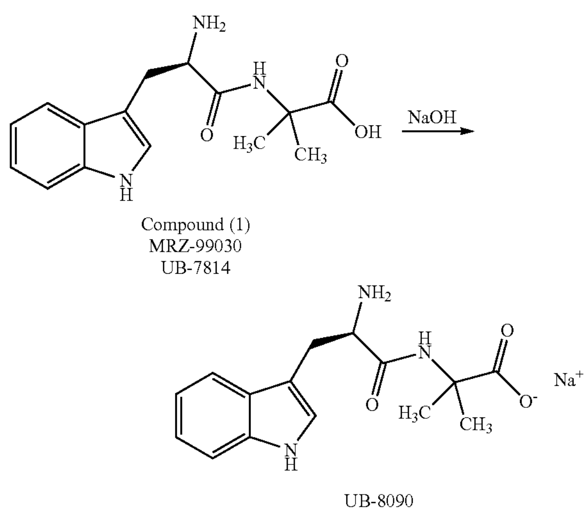

Compound (1)
MRZ-99030
UB-7814

UB-8090

Amorphous sodium salts of compound (1) (UB-08090) were synthetized successfully dissolving solid compound (1) (MRZ-99030) in stoichiometric among of aqueous NaOH solution followed by lyophilization.

Procedure for Preparation of Amorphous Sodium Salt of Compound (1) (UB-08090)

A 2 L round bottom flask was charged with 30.0 g (103.7 mmol) of compound (1) (MRZ-99030) then it was suspended in 500 mL deionized water, and 104 mL 1 M aqueous solution of NaOH was added to it. The resulting solution was lyophilized for two days. Yield: 34.0 g (109.3 mmol; >100%), HPLC: 98.92 area %

The amorphous salt was successfully crystallized from 2-propanol, n-propanol and n-butanol, no other solvents were appropriate for crystallization. According to XRPD analysis three 3 different crystal forms were detected (Form A, Form B and Form C). The crystals isolated from 2-propanol were tested for solubility, stability and hygroscopicity.

TABLE 2

| Crystallization of solvates of sodium salt of compound (1) (UB-08090) | | | | |
|---|---|---|---|---|
| Entry | Input | Raw materials/Solvent | Conditions | Observations/Remarks |
| 1 | 100 mg Amorphous sodium salt | Methanol (5 vol) | 20-25° C.<br>0-5° C.<br>−20-(−15) °C | No crystallization was observed<br>No crystallization was observed<br>No crystallization was observed |
| 2 | 100 mg Amorphous sodium salt | Ethanol (5 vol) | 20-25 °C<br>0-5° C.<br>−15° C. | No crystallization was observed<br>No crystallization was observed<br>No crystallization was observed |
| 3 | 100 mg Amorphous sodium salt | 2-Propanol (20 vol.) | 20-25° C. | white crystals formed |
| 4 | 100 mg Amorphous sodium salt | n-Propanol (20 vol.) | 20-25° C. | white crystals formed |
| 5 | 100 mg Amorphous sodium salt | n-Butanol (20 vol.) | 20-25° C. | white crystals formed |
| 6 | 100 mg Amorphous sodium salt | EtOAc (5 vol.) | 20-25° C. | oily precipitation |
| 7 | 100 mg Amorphous sodium salt | iPrOAc (5 vol.) | 20-25° C. | oily precipitation |
| 8 | 100 mg Amorphous sodium salt | Anisole (5 vol.) | 20-25° C. | oily precipitation |
| 9 | 100 mg Amorphous sodium salt | THF (5 vol.) | 20-25° C. | oily precipitation |
| 10 | 100 mg Amorphous sodium salt | 2-MeTHF (5 vol) | 20-25° C. | oily precipitation |
| 11 | 100 mg Amorphous sodium salt | $CH_3CN$ (5 vol.) | 20-25° C. | No crystallization was observed |
| 12 | 5 g Compound (1) | water/NaOH (5 vol.) | 20-25° C.<br>0-5° C. | No crystallization was observed<br>No crystallization was observed |
| 13 | 1 g Compound (1) | water/NaOH (3.5 vol.) | 20-25° C.<br>0-5° C. | No crystallization was observed<br>No crystallization was observed |
| 14 | 2 g Amorphous sodium salt | 2-Propanol (30 vol.) | 1 h/20-25° C. | white crystals formed XRPD: The sample is crystalline and consists of a single crystalline modification. (Form A) |
| 15 | 1 g Amorphous sodium salt | 2-Propanol (30 vol.) | 30 min. reflux then 1 h/20-25° C. | white crystals formed XRPD: The sample consists of the same crystalline modification with a higher crystallinity. (Form A) |
| 16 | 1 g Amorphous sodium salt | n-Propanol (30 vol.) | 1 h/20-25° C. | white crystals formed XRPD: The sample is crystalline and consist of a mixture of two crystalline modifications, (Form B), the other one is not detected in the other samples (Form C). |
| 17 | 1 g Amorphous sodium salt | n-Butanol (30 vol.) | 1 h/20-25° C. | white crystals formed XRPD: The sample is crystalline and consist of a single crystalline modification (Form B) |
| 18 | 10 g (34.56 mmol) Compound (1) | 20 w/w % aq. NaOH (1 mol. eq.)<br>2-Propanol (40 vol.) | 3-4 h/80-82° C.<br>1 h/20-25° C. | The sodium salt was formed in water with 20 w/w % aq. NaOH, 2-propanol was added to clear solution and the water was removed by azeotrope distillation. After removal of the water, the sodium salt precipitated from the 2-propanol. |
| 19 | 1 g Amorphous sodium salt | 2-Propanol (30 vol.) | 16-18 h/70-75° C. then 1-2 h/20-25° C. | XPRD: Form A |
| 20 | 1 g Amorphous sodium salt | n-Propanol (10 vol.) | 16-18 h/70-75° C. then 1-2 h/20-25° C. | XPRD: Form C |
| 21 | 1 g Amorphous sodium salt | n-Butanol (30 vol.) | 16-18 h/70-75° C. then 1-2 h/20-25° C. | XPRD: Form B |

TABLE 2-continued

| Crystallization of solvates of sodium salt of compound (1) (UB-08090) | | | | |
|---|---|---|---|---|
| Entry | Input | Raw materials/Solvent | Conditions | Observations/Remarks |
| 22 | 400 mg Amorphous sodium salt | 2-Propanol (30 vol.) | 16-18 h/70-75° C. then 1-2 h/20-25° C. | XPRD: Form A |
| 23 | 1 g Amorphous sodium salt | 0.5 mL deionized water | 20-25° C. | solubility test: clear solution |
| 24 | 100 mg Amorphous sodium salt | | 45-50° C. | Stability trials were performed at 50° C., no degradation could be observed after 48 hours. 0 h: 99.7 area % |
| 25 | 500 mg Amorphous sodium salt | | Relative humidity: 58-60% 20-25° C./24 h 20-25° C./48 h | The hygroscopicity of the salt was investigated at 58-60% relative humidity. The weight of crystals increased with 2.64% within 24 hours, 3.4% 48 hours. |

Preparation of Sodium Salt Solvates of Compound (1) by Crystallization

Sodium 2-Propanol Solvate (UB-18813)

A 2 L round bottom flask was charged with 50.0 g (172.8 mmol) of compound (1) (MRZ-99030) 75 mL deionized water and 34.6 g 20 w/w % aq. NaOH solution (6.9 g NaOH, 172.8 mmol, 1.0 eq). A light brown solution was obtained. 1500 ml 2-propanol was added and the mixture of water/2-propanol was distilled off ($T_{pot}$=110° C., $T_{head}$=80° C., final volume ~300 ml). The mixture was then cooled to room temperature resulting in a thick slurry of the amorphous sodium salt of compound (1) (UB-08090). The crystals were filtered, washed with 2-propanol and dried (50° C., vacuo). Yield: 52.8 g (169.6 mmol; 98.1%) sodium 2-propanol solvate of compound (1) (UB-18813). Residual 2-propanol: 17.8 w/w % (calculated for 1.0 eq: 16.2%). Water content (KF): 0.2 w/w %

Sodium 1-Butanol Solvate of Compound (1) (UB-18815)

A 2 L round bottom flask was charged with 50.0 g (172.8 mmol) of compound (1) (MRZ-99030) 75 mL deionized water and 34.6 g 20 w/w % aq. NaOH solution (6.9 g NaOH, 172.8 mmol, 1.0 eq). A light brown solution was obtained. 1400 ml 1-butanol was added and the mixture of water/1-butanol was distilled off ($T_{pot}$=128° C., $T_{head}$=102° C., final volume ~200 ml). The mixture was then cooled to room temperature resulting in a thick slurry of the amorphous sodium salt of compound (1) (UB-08090) the crystals were filtered, washed with 1-butanol and dried (50° C., vacuo). Yield: 56.4 g (0.181 mmol; >100%) sodium 1-butaol solvate of compound (1) (UB-18815). Residual 1-butanol: 121.3 w/w % (calculated for 1.0 eq: 19.2%). Water content (KF): 0.15 w/w %

Sodium 1-Propanol Solvate of Compound (1) (B-18814)

A 2 L round bottom flask was charged with 50.0 g (172.8 mmol) of compound (1) (MRZ-99030) 75 mL deionized water and 34.6 g 20 w/w % aq. NaOH solution (6.9 g NaOH, 172.8 mmol, 1.0 eq). A light brown solution was obtained. 1500 ml 1-propanol was added and the mixture of water/1-propanol was distilled off ($T_{pot}$=110° C., $T_{head}$=100° C., final volume ~300 ml). The mixture was then cooled to room temperature resulting in a thick slurry of sodium salt of compound (1) (UB-08090). the crystals were filtered, washed with 1-propanol and dried (50° C., vacuo). Yield: 56.6 g (0.1818 mmol; >100%) Sodium 1-propanol solvate of compound (1) (UB-18814). Residual 1-propanol: 18.5 w/w % (calculated for 1.0 eq: 16.2%). Water content (KF): 0.2 w/w %

Crystallographic Characterization of Sodium Solvates of Compound (1) (XRPD)

Several sodium and potassium solvates of compound (1) were crystallized from three different solvents in various conditions were characterized using X-ray powder diffraction (XRPD). Five crystalline modifications were identified and labeled with letters A through E. All the five modifications were indexed successfully. The lattice symmetry and unit cell parameter data are summarized in Table 2. The detailed indexing sheets are attached.

Measured solvent contents for the various crystalline forms of solvates of sodium salts of compound (1) were usually slightly higher than one mol solvent pro formula unit (1.14-1.18), suggesting that drying is incomplete—not the total amount of the measured solvent is in the crystal lattice. Solvate contents calculated from measured densities are in a good agreement with the measured figures taking into consideration the surface (extra-lattice) solvent.

TABLE 3

| Solvated densities and of sodium and potassium salt solvated of compound (1) | | | | | | | | | |
|---|---|---|---|---|---|---|---|---|---|
| | Z | V $A^3$ | $V_0$ $A^3$ | Solvate type | Solvate n/mol | Dx g/cm$^3$ | Dm g/cm$^3$ | Calculated solvate content w/w % | Measured solvent content w/w % |
| Na-Solvates Forms | | | | | | | | | |
| Form A | 4 | 1957 | 489.25 | i-propanol | 0 | 1.059 | 1.29 | 0 | 17.8 (1.12 mol) |
| | | | | | 1 | 1.264 | | 16.18 | |
| | | | | | 1.12 | 1.288 | | 17.8 | |
| | | | | | 2 | 1.468 | | 27.85 | |
| Form B | 2 | 988 | 494 | n-butanol | 0 | 1.046 | 1.31 | 0 | 21.3 (1.14 mol) |
| | | | | | 1 | 1.296 | | 19.23 | |
| | | | | | 1.06 | 1.311 | | | |
| | | | | | 2 | 1.545 | | 32.26 | |
| Form C | 4 | 1986 | 496.5 | n-propanol | 0 | 1.041 | 1.30 | 0 | 18.5 (1.18 mol) |
| | | | | | 1 | 1.242 | | 16.18 | |
| | | | | | 1.30 | 1.302 | | | |
| | | | | | 2 | 1.443 | | 27.85 | |
| K-Solvate Forms | | | | | | | | | |
| Form D | 4 | 2051 | 512.5 | i-propanol | 0 | 1.060 | — | 0 | |
| | | | | | 1 | 1.255 | | 15.51 | |
| | | | | | 2 | | | 26.85 | |
| Form E | 4 | 2103 | 525.5 | n-butanol | 0 | 0.983 | — | 0 | |
| | | | | | 1 | 1.217 | | 18.46 | |
| | | | | | 2 | 1.452 | | 31.17 | |

Z is the number of formula units (molecules) per unit cell, V is the volume of the unit cell (Å$^3$), $V_0$ is the lattice volume for one formula unit ($V_0$=V/Z, Å$^3$), Dx is the calculated density (from the volume and content of the unit cell), Dm is the measured density.

DSC analysis of the sample of sodium 2-propanol solvate of compound (1) (UB-18813) was performed by repeated heating and cooling cycles: the sample was carefully heated above the melting point then, after cooling to ambient temperature, the heating program was repeated. The first curve showed a sharp peak of melting of the sample and a light brown amorphous residue was obtained. This sample was analyzed by TLC and no decomposition of the dipeptide was found. During the second heating cycle the peak of melting was missing, only the high temperature decomposition was observed.

DSC Analysis of Solvates of Sodium Salt of Compound (1)

DSC curve of the solvate crystals were recorded using 10° C./min heating rate. Sharp melting points were found in all cases.

TABLE 4

| DSC analysis of sodium salt of compound (1) solvates | |
|---|---|
| Solvent/Solvate | Mp (determined by DSC) |
| 2-Propanol UB-18813 | 140.8° C. |
| 1-Butanol UB-18815 | 141.0° C. |
| 1-Propanol UB-18814 | 126.0° C. |

DSC analysis of the sample of sodium 2-propanol solvate of compound (1) (UB-18813) was performed by repeated heating and cooling cycles: the sample was carefully heated above the melting point then, after cooling to ambient temperature, the heating program was repeated. The first curve showed a sharp peak of melting of the sample and a light brown amorphous residue was obtained. This sample was analyzed by TLC and no decomposition of the dipeptide was found. During the second heating cycle the peak of melting was missing, only the high temperature decomposition was observed. The analysis proved that melting of the sample is associated with loss of solvent and it results in amorphous sodium salt of compound (1) (UB-08090) without decomposition.

Solubility of Solvates of Sodium Salts of Compound (1)

Solubility of sodium 2-propanol solvate of compound (1) (UB-18813) was tested. Deionized water was stirred at room temperature and sodium 2-propanol solvate of compound (1) (UB-18813) was added in small portions. sodium 2-propanol solvate of compound (1) (UB-18813) dissolves readily and forms 70 w/w % (4.55 g salt was dissolved in 2 ml deionized water) as a honey-like viscous solution was obtained. The solution can dissolve further amount of sodium 2-propanol solvate salt of compound (1) (UB-18813), because of the high viscosity of the solution we did not add more salt.

Sodium 2-propanol solvate salt of compound (1) (UB-18813) has surprisingly high solubility in water, it is readily soluble at 70 w/w % or higher. This corresponds to a more than 50-fold increase of solubility compared to the zwitter ionic form of compound (1).

Thermal stability of the 70 w/w % solution of 2-propanol solvate of compound (1) (UB-18813) in water was tested. The solution stirred at 50° C. under N2 atmosphere for 24 hrs and the stability was monitored by TLC analysis (silica, butanol-acetic acid 4:1:1). No traces of decomposition were observed within 24 hrs.

Solubility of Amorphous Form of Compound (1)

Solubility of amorphous compound (1) was determined by dissolution it in deionized water at 24° C., the suspension was stirred at 1 hr and filtered, filtered and an aliquot of the filtrate was evaporated to dryness. Solubility at 24° C.: 1.3 w/w %. Preparation of the amorphous potassium salt of compound (1) (UB-08091)

Scheme 2 - Synthetic scheme for preparation of potassium salt of compound (1)

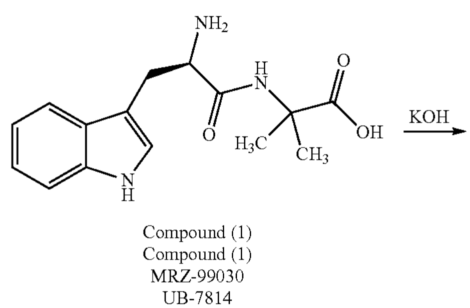

Compound (1)
Compound (1)
MRZ-99030
UB-7814

-continued

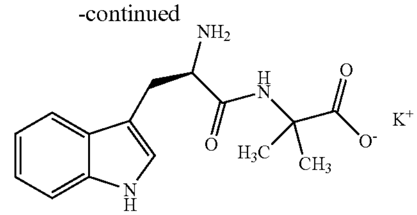

UB-8091

Amorphous potassium salts of compound (1) were synthetized successfully using aqueous solution of KOH followed by lyophilization.

Preparation Procedure

A 2 L round bottom flask was charged with 30.0 g (103.7 mmol) of compound (1) (MRZ-99030) and it was suspended in 500 mL deionized water then 104 mL 1 M aqueous solution of KOH was added to it. The resulting solution was lyophilized for two days. Yield: 35.2 g (107.5 mmol; >100%) amorphous form of potassium salt of compound (1) (UB-08091).

Crystallization of the Potassium Salt

The amorphous salt was successfully crystallized from 2-propanol and n-butanol, no other solvents were appropriate for crystallization. According to XRPD we could conclude two crystallin forms appeared. (Form D and Form E).

TABLE 3

Crystallization of solvates of potassium salts of compound (1)

| Entry | Input | Raw materials/Solvent | Conditions | Observations/Remarks |
|---|---|---|---|---|
| 1 | 100 mg amorphous potassium salt | 2-Propanol (10 vol.) | 20-25° C. | No crystallization was observed |
| | | | −15° C./2 days | white crystals formed, not dissolved back at 20-25° C. |
| 2 | 100 mg amorphous potassium salt | n-Butanol (10 vol.) | 20-25° C. | No crystallization was observed |
| | | | −15° C./2 days | white crystals formed, not dissolved back at 20-25° C. |
| 3 | 1 g amorphous potassium salt | 2-Propanol (20 vol.) | 20-25° C. | The potassium salt was crystallized at 20-25° C. using seed crystals from experiment |
| 4 | 1 g potassium salt amorphous | n-Propanol (10 vol.) | 20-25° C. | No crystallization was observed |
| | | | −15° C./6 days | No crystallization was observed |
| 5 | 1 g amorphous potassium salt | n-Butanol (10 vol.) | 20-25° C. | The potassium salt was crystallized at 20-25° C. using seed crystals from experiment XRPD: Form E |

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A crystalline form of a solvate salt of compound (I), wherein said solvate is a $C_3$-$C_4$ alcohol thereof, wherein said salt is an alkali salt, wherein said alkali salt is selected from sodium and potassium.

2. A crystalline form according to claim 1, wherein said solvate is selected from 1-propanol, 2-propanol, 1-butanol, iso-butanol and any combinations thereof.

3. A crystalline form according to claim 1, wherein said solvate salt compound (1), is a compound of formula (I):

(I)

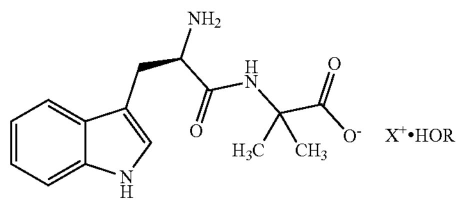

Wherein $X^+$ is an alkali cation; and R is a $C_3$-$C_4$ alkyl.

4. A crystalline form according to claim 3, wherein X+ is sodium (Na+) or potassium (K+) cation.

5. A crystalline form according to claim 1 wherein said solvate salt compound (1) is a solvated sodium salt selected from:

(2)

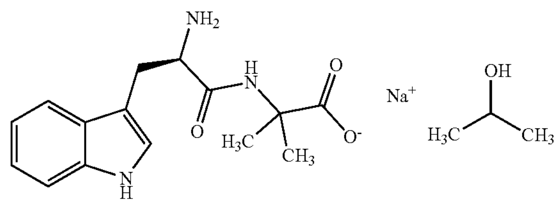

(3)

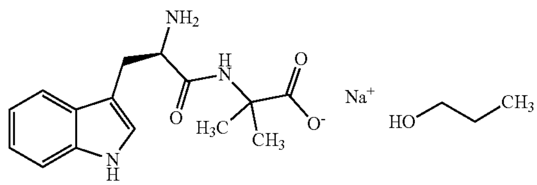

(4)

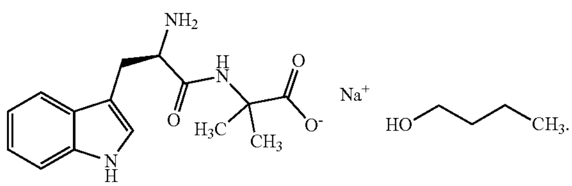

6. A crystalline form according to claim 1 wherein said solvate salt compound (1) is a solvated K salt selected from:

(5)

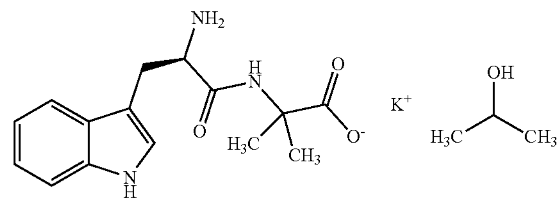

(6)

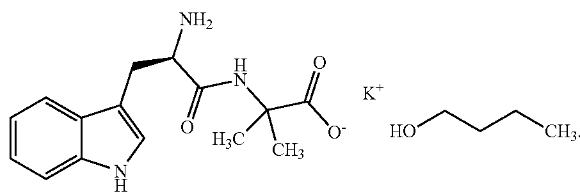

7. A crystalline form according to claim 1, wherein said crystalline form is selected from a sodium 2-propanol solvate of compound (1) having crystalline form A, a sodium 1-butanol solvate of compound (1) having crystalline form B, or a sodium 1-propanol solvate of compound (1) having crystalline form C.

8. A crystalline form according to claim 1 having purity of at least 99.7%.

9. A crystalline form according to claim 1 having water solubility of 2.3 g/ml.

10. A pharmaceutical composition comprising at least one crystalline form or prepared from at least one crystalline form according to claim 1.

11. A pharmaceutical composition according to claim 10, wherein said composition is suitable for ocular administration, oral administration, nasal administration, or any combination thereof.

12. A method of treating an amyloid-associated disease in a subject suffering therefrom, said method comprising administering to said subject a pharmaceutical composition comprising at least one crystalline form or prepared from at least one crystalline form of a solvate salt compound (1), wherein said solvate is a $C_3$-$C_4$ alcohol thereof, (1)

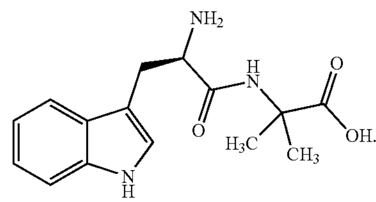

13. A method of treating an amyloid associated disease according to claim 12, wherein said amyloid-associated disease is selected from type II diabetes mellitus, Alzheimer's disease (AD), early onset Alzheimer's disease, late onset Alzheimer's disease, Alzheimer's dementia, Parkinson's disease, SAA amyloidosis, hereditary Icelandic syndrome, multiple myeloma, medullary carcinoma, aortic medical amyloid, insulin injection amyloidosis, prion-systematic amyloidosis, chronic inflammation amyloidosis, Huntington's disease, senile systemic amyloidosis, pituitary gland amyloidosis, hereditary renal amyloidosis, familial British dementia, Finnish hereditary amyloidosis, familial non-neuropathic amyloidosis, amyloid-related ocular diseases and disorders such as glaucoma and age-related macular degeneration (AMD, dry form and wet form), prion diseases including prion-related encephalopathies, scrapie of sheep and goats and bovine spongiform encephalopathy (BSE) of cattle and human prion diseases including Kuru disease, Creutzfeldt-Jakob disease (CJD), Gerstmann-Sträussler-Scheinker disease (GSS), and fatal familial insomnia (FFI).

* * * * *